(12) United States Patent
Chang et al.

(10) Patent No.: US 9,864,032 B2
(45) Date of Patent: Jan. 9, 2018

(54) MAGNETIC RESONANCE IMAGING SYSTEM

(75) Inventors: Hsu Chang, Fremont, CA (US); Ching Yao, Miaoli County (TW); San-Chao Hwang, Miaoli County (TW)

(73) Assignee: National Health Research Institutes, Zhunan Town (TW)

( * ) Notice: Subject to any disclaimer, the term of this patent is extended or adjusted under 35 U.S.C. 154(b) by 1780 days.

(21) Appl. No.: 12/652,450

(22) Filed: Jan. 5, 2010

(65) Prior Publication Data

US 2011/0166437 A1    Jul. 7, 2011

(51) Int. Cl.
| | |
|---|---|
| A61B 5/055 | (2006.01) |
| G01R 33/48 | (2006.01) |
| A61N 7/02 | (2006.01) |
| G01R 33/34 | (2006.01) |
| G01R 33/36 | (2006.01) |
| G01R 33/341 | (2006.01) |
| G01R 33/3415 | (2006.01) |

(52) U.S. Cl.
CPC .......... *G01R 33/4814* (2013.01); *A61B 5/055* (2013.01); *A61N 7/02* (2013.01); *G01R 33/34084* (2013.01); *G01R 33/365* (2013.01); *G01R 33/341* (2013.01); *G01R 33/3415* (2013.01)

(58) Field of Classification Search
CPC ............ G01R 33/34084; G01R 33/341; G01R 33/3415; G01R 33/365; G01R 33/4814; A61B 5/055; A61N 7/00; A61N 7/02
See application file for complete search history.

(56) References Cited

U.S. PATENT DOCUMENTS

| | | | | |
|---|---|---|---|---|
| 4,782,298 A | * | 11/1988 | Arakawa ............ | G01R 33/3657 324/318 |
| 4,891,596 A | * | 1/1990 | Mitomi ......................... | 324/318 |
| 4,897,604 A | * | 1/1990 | Carlson ............ | G01R 33/34053 324/318 |
| 5,041,791 A | * | 8/1991 | Ackerman et al. .......... | 324/318 |
| 5,435,302 A | | 7/1995 | Lenkinski et al. | |

(Continued)

FOREIGN PATENT DOCUMENTS

| | | |
|---|---|---|
| DE | 9407862 | 9/1995 |
| EP | 0412824 | 2/1991 |

(Continued)

OTHER PUBLICATIONS

Hashizume, MRI-guided laparoscopic and robotic curgery for malignancies, Int J Clin Oncol (2007) 14:94-98.*

(Continued)

*Primary Examiner* — Ruth S Smith
(74) *Attorney, Agent, or Firm* — Knobbe, Martens, Olson & Bear, LLP

(57) ABSTRACT

A magnetic resonance imaging system to be used over a target area of a subject includes first and second RF coils for receiving an RF signal from the subject. The first RF coil is fixed to a position device and movable over the target area of subject. The second RF coil is larger than the first RF coil and has a larger field of view than the first RF coil. The system further includes an image processing device programmed to process RF signals coupled from the first RF coil and the second RF coil to form an MRI image.

6 Claims, 10 Drawing Sheets

(56) References Cited

U.S. PATENT DOCUMENTS

| | | | |
|---|---|---|---|
| 5,461,314 | A | 10/1995 | Arakawa et al. |
| 5,752,515 | A * | 5/1998 | Jolesz et al. ............... 600/458 |
| 5,777,474 | A * | 7/1998 | Srinivasan ................ 324/318 |
| 5,905,378 | A | 5/1999 | Giaquinto et al. |
| 6,144,203 | A | 11/2000 | Richard et al. |
| 6,184,684 | B1 | 2/2001 | Dumoulin et al. |
| 6,246,895 | B1 * | 6/2001 | Plewes ................ A61B 8/00 324/309 |
| 6,591,128 | B1 * | 7/2003 | Wu ................ G01R 33/34084 324/318 |
| 6,836,117 | B2 | 12/2004 | Tamura et al. |
| 6,906,518 | B2 * | 6/2005 | Leussler ............ G01R 33/3628 324/318 |
| 6,980,002 | B1 * | 12/2005 | Petropoulos ....... G01R 33/3415 324/309 |
| 2001/0043068 | A1 * | 11/2001 | Lee ............... 324/309 |
| 2002/0138001 | A1 | 9/2002 | Kroeckel |
| 2004/0030241 | A1 * | 2/2004 | Green et al. ............... 600/422 |
| 2007/0016003 | A1 * | 1/2007 | Piron ................ A61B 5/415 600/415 |
| 2008/0015430 | A1 | 1/2008 | Takamori |
| 2009/0027053 | A1 | 1/2009 | Decke |
| 2009/0079431 | A1 * | 3/2009 | Piferi et al. ............... 324/318 |
| 2011/0026801 | A1 * | 2/2011 | Dohata et al. ............. 382/131 |

FOREIGN PATENT DOCUMENTS

| | | |
|---|---|---|
| EP | 0558029 | 9/1993 |
| WO | WO 93/08733 | 5/1993 |
| WO | 02/39135 | 5/2002 |

OTHER PUBLICATIONS

Ohliger, Michael A. and Daniel K. Sodickson, "An introduction to coil array design for parallel MRI," NMR in Biomedicine,19:300-315 (2006).

Spence, Dan K. and Steven M. Wright, "Comparison of Local and Global Arrays for MRI," Concepts Magn. Reson Part B (Magn Reson Enginering) 31B:86-94 (2007).

Roemer et al., "The NMR Phased Array," Magnetic Resonance in Medicine, 16: 192-225 (1990).

Venook et al., "Automatic Tuning of Flexible Interventional RF Receiver Coils," Magnetic Resonance in Medicine, 54: 983-993 (2005).

Blaimer et al., "Smash, Sense Pils, Grappa: How to Choose the Optimal Method," Top Magn Reson Imaging,15:223-236 (2004).

Hoge et al., "A Tour of Accelerated Parallel MR Imaging from a Linear Systems Perspective," Concepts Magn Reson Part A 27A:17-37 (2005).

* cited by examiner

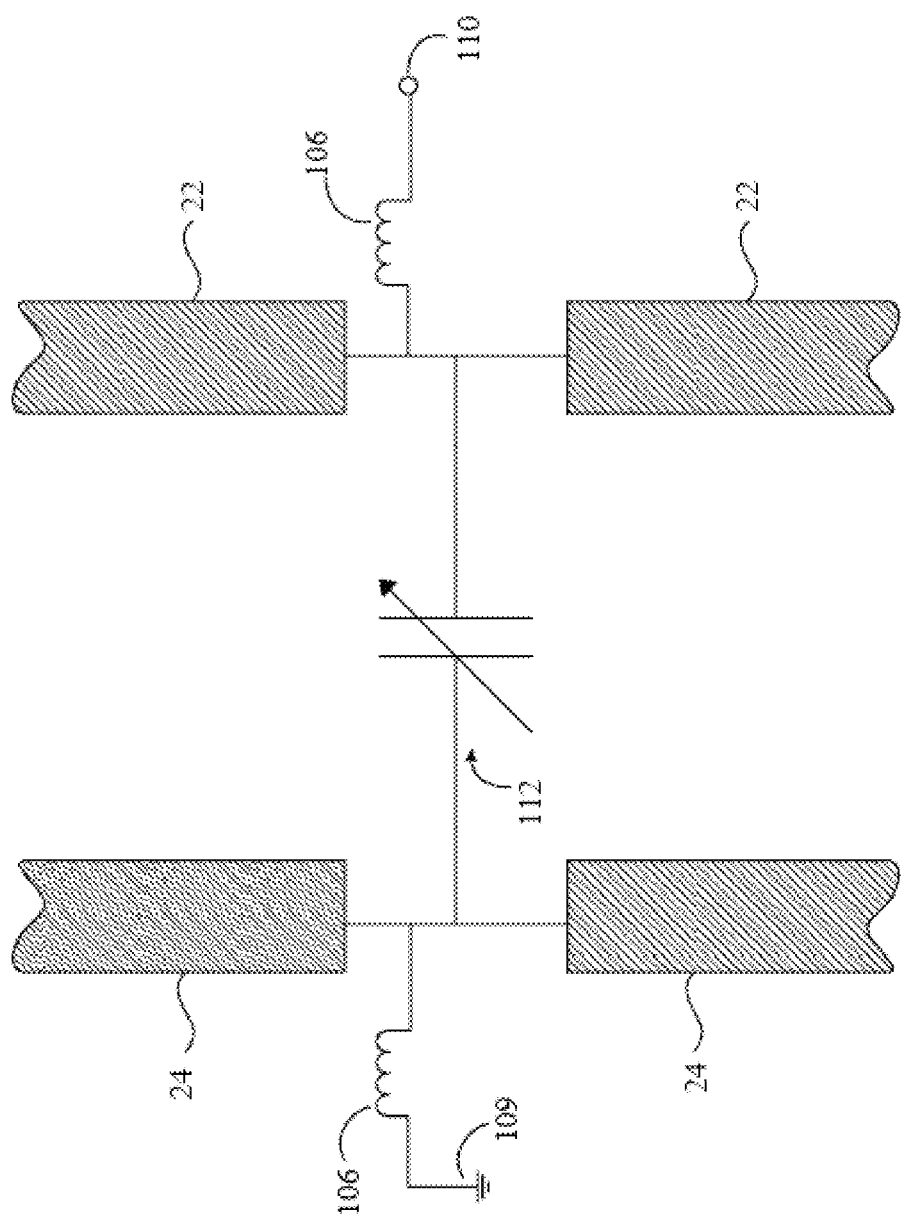

MAGNETIC RESONANCE IMAGING SYSTEM

FIELD OF DISCLOSURE

This disclosure relates to medical imaging systems, and in particular, to MRI systems.

BACKGROUND OF THE INVENTION

Magnetic resonance imaging (MRI) is a clinically important medical imaging modality due to its ability to non-invasively provide highly detailed anatomical images with exquisite soft-tissue contrast. These properties of MRI make it a major tool for image-guided biopsy and image-guided therapy using high intensity focused ultrasound (HIFU), radiofrequency (RF) waves, microwaves, cryotherapy, laser, and radiation.

During the MRI process, a subject is placed in a static magnetic field that remains constant. The magnetic moment of nuclei within the subject becomes aligned with the magnetic field. The subject is also exposed to an oscillating magnetic field having a selected frequency in the RF range of the electromagnetic spectrum. This field causes the nuclei within the subject to resonate. After the RF radiation is switched off, the nuclei continue to resonate. This results in the emission of RF radiation from the resonating nuclei. The emission is detected as an MRI signal. An RF receive coil may also be used to receive the resonating emissions from the subject.

For an RF receive coil with a fixed geometry, the signal-to-noise ratio of magnetic resonance signals from a sample increases approximately linearly with the magnetic field. The closer the RF receive coil is to the sample, the larger the signal-to-noise ratio. Thus, for low fields it is very important that the receive coil be close to the body. The greater the distance between the coil and body, the poorer the MRI image. Therefore, in a typical MR-guided interventional procedure, the subject may be placed in a volume receive coil, or near a surface receive coil laid over the region to be imaged, or a phased array coil may be used.

The placement of the coil is set at the start of the procedure. The coil is made large enough to cover the entire treatment area, so that it can remain stationary throughout the procedure. There are drawbacks to such a setup. With large coils, image quality and speed of MRI will suffer, and accuracy and safety of therapy will be affected. On the other hand, when a smaller coil is set over large organs such as liver, the therapeutic device may need to moved over a large area. The coil will then be an impediment to the movement. The movability of the coil should be considered to design a better MRI system.

SUMMARY OF THE INVENTION

In one aspect, the invention features a magnetic resonance imaging system to be used over a target area of a subject. Such a system includes first and second RF coils for receiving an RF signal from the subject. The first RF coil is fixed to a position device and movable over the target area of subject. The second RF coil is larger than the first RF coil and has a larger field of view than the first RF coil. The system further includes an image processing device programmed to process RF signals coupled from the first RF coil and the second RF coil to form an MRI image.

In one embodiment, the first RF coil and the second RF coil are located on different sides of the subject and face each other.

In another embodiment, the first and second RF coils are configured to sandwich the subject therebetween and to face each other.

Other embodiments include subject bed. In these embodiments, the second RF coil is located on the subject bed and disposed such that, in use, the subject lays over the second RF coil and the first RF coil is over the subject.

Additional embodiments include those in which the first RF coil is configured to follow a therapeutic device while the therapeutic device performs on the target area of the subject. In some but not all of these embodiments, the first RF coil is ring shaped and defines an inner opening space larger than a head of the therapeutic device.

Yet other embodiments include those in which the first RF coil includes a surface coil, others in which the second RF coil includes a phased array coil, and still others in which the first RF coil and the second RF coil include at least one of a single loop, a quadrature loop, and an array coil, Among the embodiments are those that also have decoupling circuitry to eliminate coupling between the first RF coil and the second RF coil or within the second RF coil.

Yet other embodiments include those having a parallel processing unit to process RF signals coupled from the first RF coil and the second RF coil parallel to form the MRI image.

In other embodiments, the second RF coil includes a flexible array of coils forming a belt for wrapping around the subject.

In another aspect, the invention features a magnetic resonance imaging system to be used during medical treatment over a target area of a subject. Such a system includes a therapeutic device for delivering energy to the subject, as well as first and second RF coils for receiving RF signals from the subject. The first RF coil is fixed to a positioning device and defines an open space in its center that is sufficient to allow a head end of the therapeutic device to pass through. The second RF coil is larger than the first RF coil and has a larger field of view than the first RF coil. The system further includes an image processing device programmed to process RF signals coupled from the first RF coil and the second RF coil to form an MRI image.

Embodiments of the above system include those in which first RF coil and the second RF coil are configured to sandwich the subject between them and to face each other.

A variety of RF coils can be used. For example, there are embodiments of the system in which the first RF coil and the second RF coil include one of a single loop, a quadrature loop and an array of coils. There are also embodiments in which the first RF coil includes a surface coil. And there are still other embodiments in which the second RF coil includes a phased array of coils, in which the first RF coil is ring shaped, and in which the second RF coil includes a phased array of coils having a plurality of coils, at least two of the coils being inductance coupled and wherein at least two of the coils are controlled by a DC controlled capacitor.

In some embodiments, the second RF coil includes a flexible array of coils that forms a belt for wrapping around the subject.

Some embodiments of the system also include a subject bed. In these embodiments, the second RF coil is located on the subject bed such that when the system is in use, the subject lays over the second RF coil and the first RF coil is over the subject.

In additional embodiments, the first RF coil is adapted to follow a therapeutic device while the therapeutic device delivers energy to the target area of the subject.

Yet other embodiments include decoupling circuitry to eliminate coupling between the first RF coil and the second RF coil or within the second RF coil.

Other embodiments include a parallel processing unit programmed to process, in parallel, RF signals coupled from the first RF coil and the second RF coil.

The system can also include, in some embodiments, a control unit programmed to receive the MRI image and to guide the therapeutic device to perform the medical treatment in real time.

In some embodiments, the MRI image is used as reference information by the therapeutic device during performance of the medical treatment.

In another aspect, the invention features a magnetic resonance imaging system to be used during medical treatment over a target area of a subject. Such a system includes a therapeutic device for delivering energy to the subject, a flexible RF coil belt for wrapping over a trunk of the subject to receive an RF signal from the subject, and an image processing device programmed to process RF signals coupled from the flexible RF coil belt to form an MRI image. The coil belt includes first, second, third, and fourth RF coils. The first RF coil defines an open space in a center thereof. This open space is sized to allow a head end of the therapeutic device to pass through it. The second RF coil is inductance coupled to the first RF coil. The third RF coil is electrically coupled to the fourth RF coil when the flexible RF coil belt is wrapped over the trunk One embodiment also includes rotating means located between the flexible RF coil belt and the trunk of the subject to facilitate rotation of the flexible RF coil belt around the trunk of the subject.

Other and further aspects and features of the invention will be evident from reading the following detailed description of the drawings, which is intended to illustrate, not limit, the scope of the attached claims.

BRIEF DESCRIPTION OF THE DRAWINGS

Various embodiments are described and illustrated herein with reference to the drawings in which like items are indicated by the same reference numeral, and in which:

FIG. 5B is a circuit diagram of another embodiment of decoupling circuit between two overlapped circular surface coils;

DETAILED DESCRIPTION

There are three kinds of magnetic fields applied in an MRI system: main fields or static fields, gradient fields, and RF fields. The static field is an intense and highly uniform magnetic field over the entire region to be imaged. The ideal static field must be extremely uniform in space and constant in time. In operation, an auxiliary electromagnet is used to enhance the spatial uniformity of the static field. Three gradient fields, one each for the x, y, and z directions are used to encode position information into the NMR signal and to apply a Fourier transform to this signal to calculate the image intensity value for each pixel. In operation, the gradient coil provides a linearly variable magnetic field that distinguishes the location of RF signals generated at different locations of the subject. The RF coil could be used for two essential purposes: transmitting and receiving signals. The coil radiates energy into a subject at a specific frequency to generate a population of nuclear magnetic spins within the subject. The spin is generated by a rotating magnetic field having an amplitude that is proportional to the static magnetic field and that rotates at the Larmor frequency. While the coil is used as a receiver, it detects a response RF signal generated from the spin.

Figure 1:
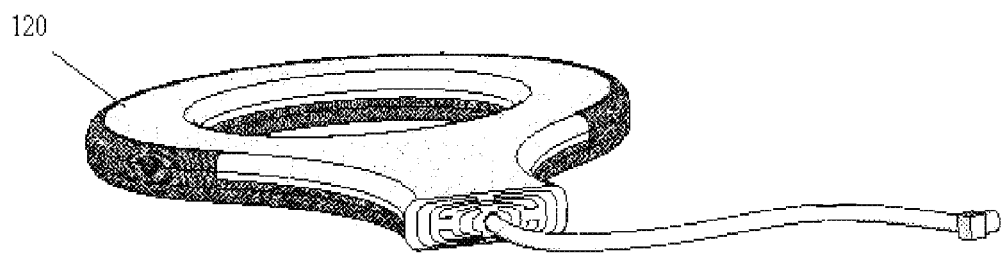
FIG. 1. is a surface coil.

Three kinds of RF coils are commonly used in the MRI system: body coils, head coils and surface coils. Body and head coils are located between the subject and the gradient coils and are designed to produce an RF magnetic field that is uniform across the region to be imaged. Head and body coils are large enough to surround the region being imaged. Body coils can have a large enough diameter (50 to 60 cm) to entirely surround the subjects' body. In contrast, a surface coil is a smaller coil designed to image a restricted region, i.e. the area of interest. Surface coils come in a wide variety of shapes and sizes and can provide a higher SNR over the head and body coils within that restricted region. One example of a surface coil is a flat surface coil 120, as shown in FIG. 1. Such a coil 120 can be put very near the region to be imaged and have a good signal-to-noise ratio (SNR), especially in the center of the RF coil. The signal received at the center is strongest and signal strength decays as the distance from the center point increases. The field of view (FOV) is thus limited to a certain small range.

MRI systems have been used for diagnostic information for many years. Recent research and study have revealed a strong interest in performing image-guided, invasive surgical procedures. MRI data, which is capable of providing excellent soft-tissue contrast and accurate position information, is often provided to a surgeon prior to surgery, for example prior to performing a biopsy. However it is preferable to generate a real-time MRI image during surgery. One such system, which is disclosed herein, combines thermal ablation surgery and MRI scanning.

Thermal ablation includes heating tissue with RF energy, with microwave energy, with focused ultrasound, or with laser light. Of these four methods, focused ultrasound is particularly useful because of its ability to non-invasively ablate human tumor tissue.

In the illustrated embodiment, high-intensity focused ultrasound (HIFU) is delivered via a concave transducer that focuses it into an ultrasound beam. One example of such HIFU can focus distance to a depth of 10 cm and produce a focal lesion with a length of 10 mm and a cross sectional diameter of 2 mm. HIFU causes cells to oscillate, thus generating heat through friction in quantities sufficient to destroy them. A useful feature of HIFU is its ability to produce a lesion having a very sharp profile, which in turn enables it to leave non-target tissue undamaged. HIFU can be applied externally, and is therefore a non-invasive surgical technique.

Figure 2:
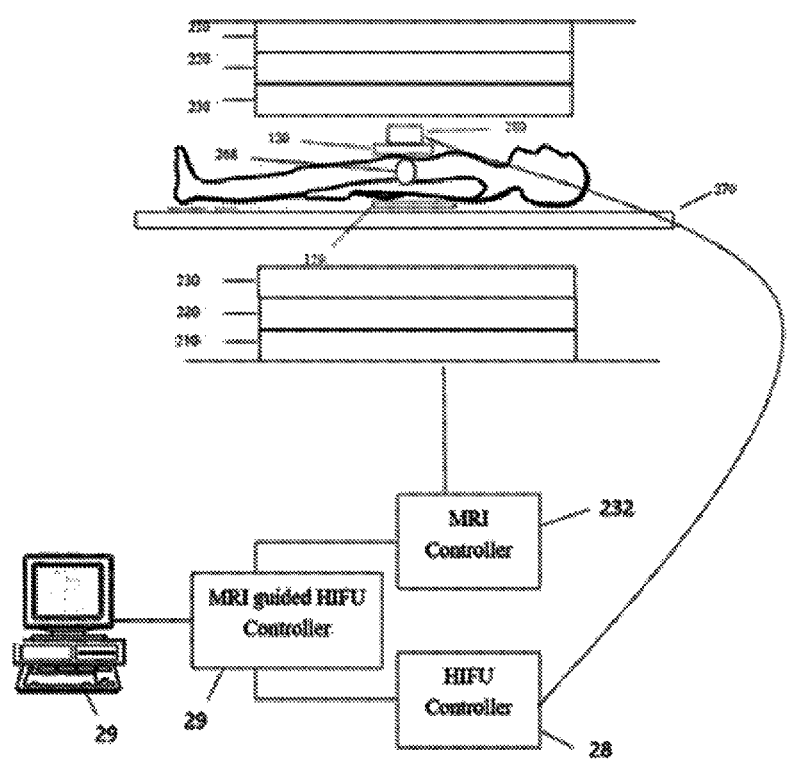
FIG. 2. is a system diagram to show an exemplary MR-Guided HIFU system.

FIG. 2 shows an example of an MR-guided HIFU system. The MR image system includes magnets 210 to impose a static magnetic field, gradient coils 220 for imposing spatially distributed magnetic fields in the three orthogonal coordinates, and RF coils 230 to receive RF signals. The signal received by the RF coils 230 is transmitted to an MRI controller 232 and is further reconstructed into image displayed on a display console connected to a computer 296. The HIFU treatment system includes an HIFU transducer 280 and an HIFU controller 282. Both the MRI Controller 232 and the HIFU controller 282 can communicate with an MRI guided HIFU Controller 290.

In use, the subject 260 lays on a table 270. Although not shown in this FIG. 2, the HIFU transducer 280 is under control of an HIFU controller 282 and/or an MRI guided HIFU Controller 290 to transmit focused ultrasound on target tissue 268 within the subject 260. The computer 296 is used by medical professionals to adjust the system, plan treatment procedures, and to monitor the therapy in real-time, and to carry out image processing tasks, such as processing data received from the RF coils and reconstructing an image on the basis thereof.

An improved MR-guided HIFU system employs a circularly-shaped surface coil 120, as shown in FIG. 1, as an RF coil 230 in FIG. 2. Unlike conventional MR-Guided HIFU systems, neither the surface coil 120 nor the HIFU transducer 280 are fixed to the table 270. Instead, both the surface coil 120 and the HIFU transducer 280 are capable of movement relative to each other. In particular, the HIFU transducer 280 has a head capable of passing through the center hole of the surface coil 120. One embodiment of the surface coil 120 has a 16 cm inner diameter and a thickness of 35 µm. In this embodiment, the diameter of the transducer head is less than 16 cm. Moreover, in order to avoid interference with the movement of the therapeutic device, the surface coil 120 is capable of moving together with the HIFU transducer 280. In another embodiment, the therapeutic device and the surface coil 120 are confocal in the sense that the therapeutic device and the coil will always cover the same localized spatial region.

The surface coil 120 need not be perfectly circular. A squared-ring shaped surface coil with an inner diameter large enough to accommodate passage of the transducer would be another example of a suitable surface coil 120. Other surface coils 120 having an equivalent share or orientation can also be used.

A single surface coil 120 can only effectively image a limited region whose dimensions are comparable to the diameter of the surface coil. In order to improve the configuration of the system and to enlarge the FOV ("field-of-view"), an alternative design combines a surface coil 120 and a flexible coil 129.

Figure 3:
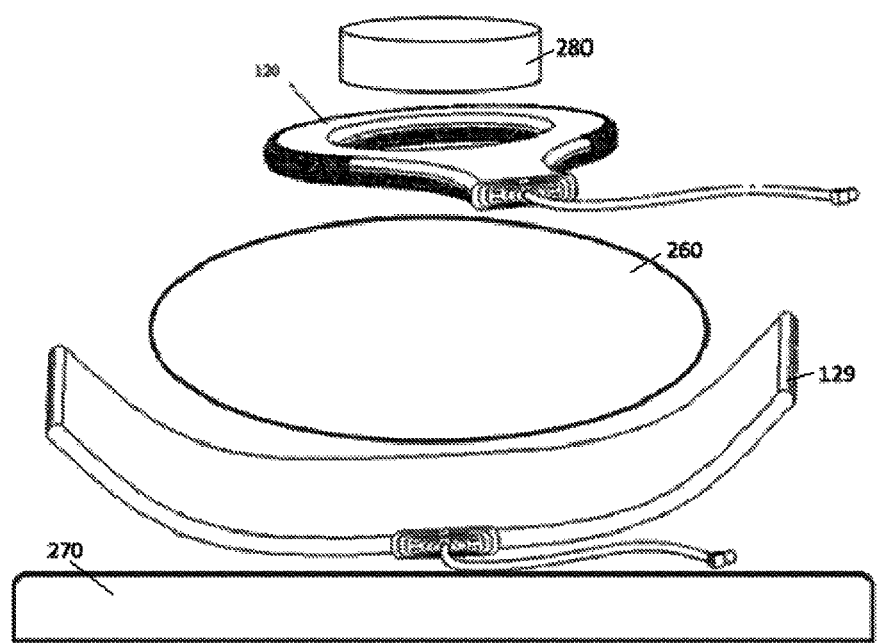
FIG. 3 is a combination of RF coils.

As shown in FIG. 3, a subject is sandwiched between a surface coil 120 and a flexible coil 129, with the flexible coil 129 being larger than the circular shaped coil 120. The flexible coil 129 can be wrapped around the subject like a belt. In some embodiments, the circumference of the flexible coil 129 is adjustable to accommodate subjects with varying girths, and its geometry is suited for fitting over the lower abdomen. The flexible coil 129 below the posterior side can be a flexible phased array of coils. The RF signals received from the small surface coil 120 and from each flexible coil of the flexible phased array of coils are each connected to respective preamplifiers for further processing.

For an RF receive coil with a fixed geometry, the greater the distance between the coil and body, the poorer the MRI image. Therefore, it is important that the receive coil be close to the body during its operation. The phased array arranges multiple coils with fixed geometry to form a large scaled geometry.

When coils couple inductively, the loops resonate as a single structure. In such cases, it can be difficult to match the impedance of each element simultaneously to the receiver circuitry. Several methods can be used to remove the effects of this mutual inductance. One method is to adjust the overlap of adjacent coils to generate a zero magnetic flux between adjacent coils, thus causing the mutual inductance to go to zero. Another method is to use an RF tuning/matching circuit in the array coils to match MRI RF coil impedance. Yet another method is to use a butterfly shaped connecting section to eliminate mutual inductance between adjacent coils. Further methods include a redesign of preamplifiers or an enhancement of the post-processing ability.

Figure 4:
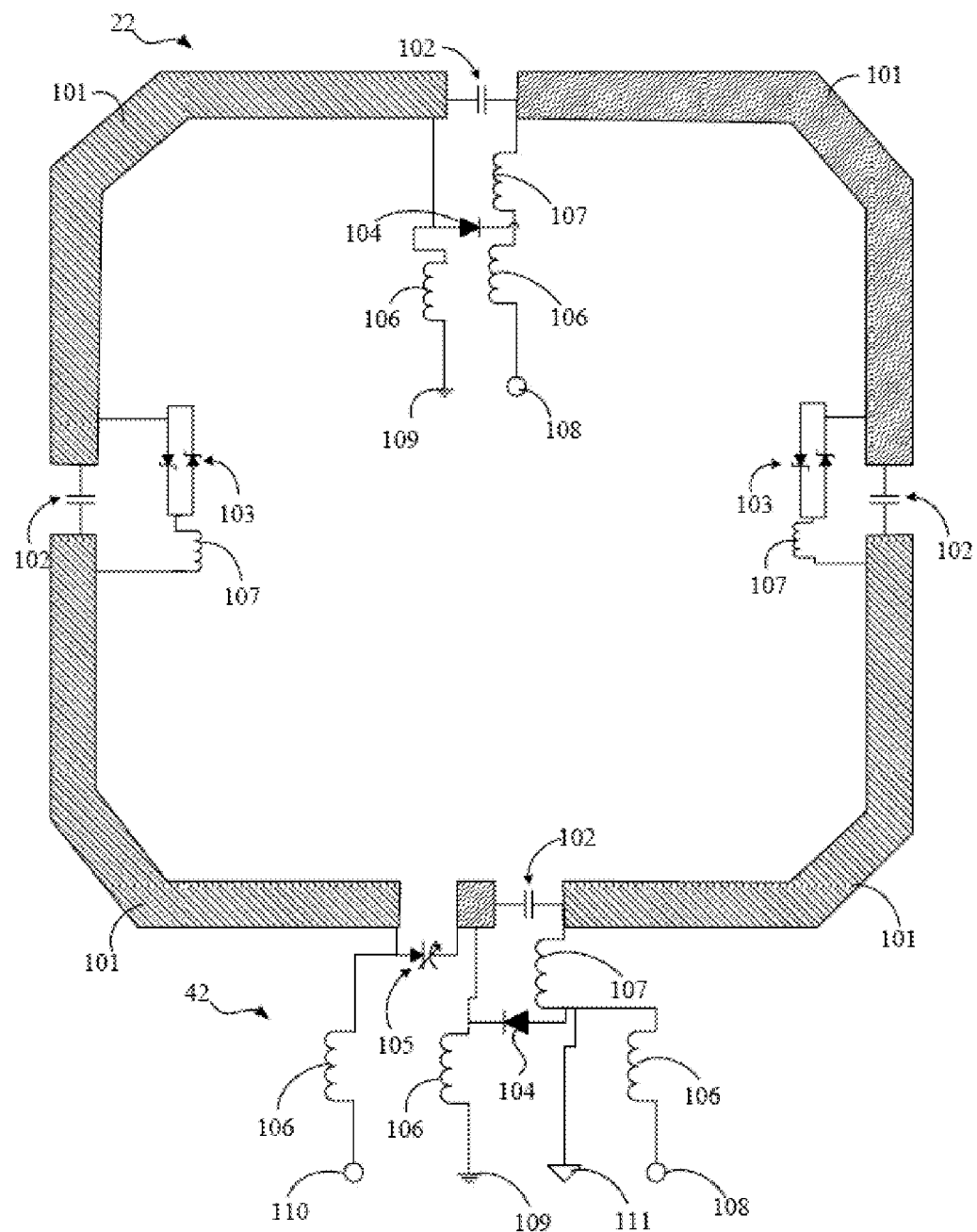
FIG. 4 is a circuit diagram of a receive-only circular surface coil.
Figure 5A:
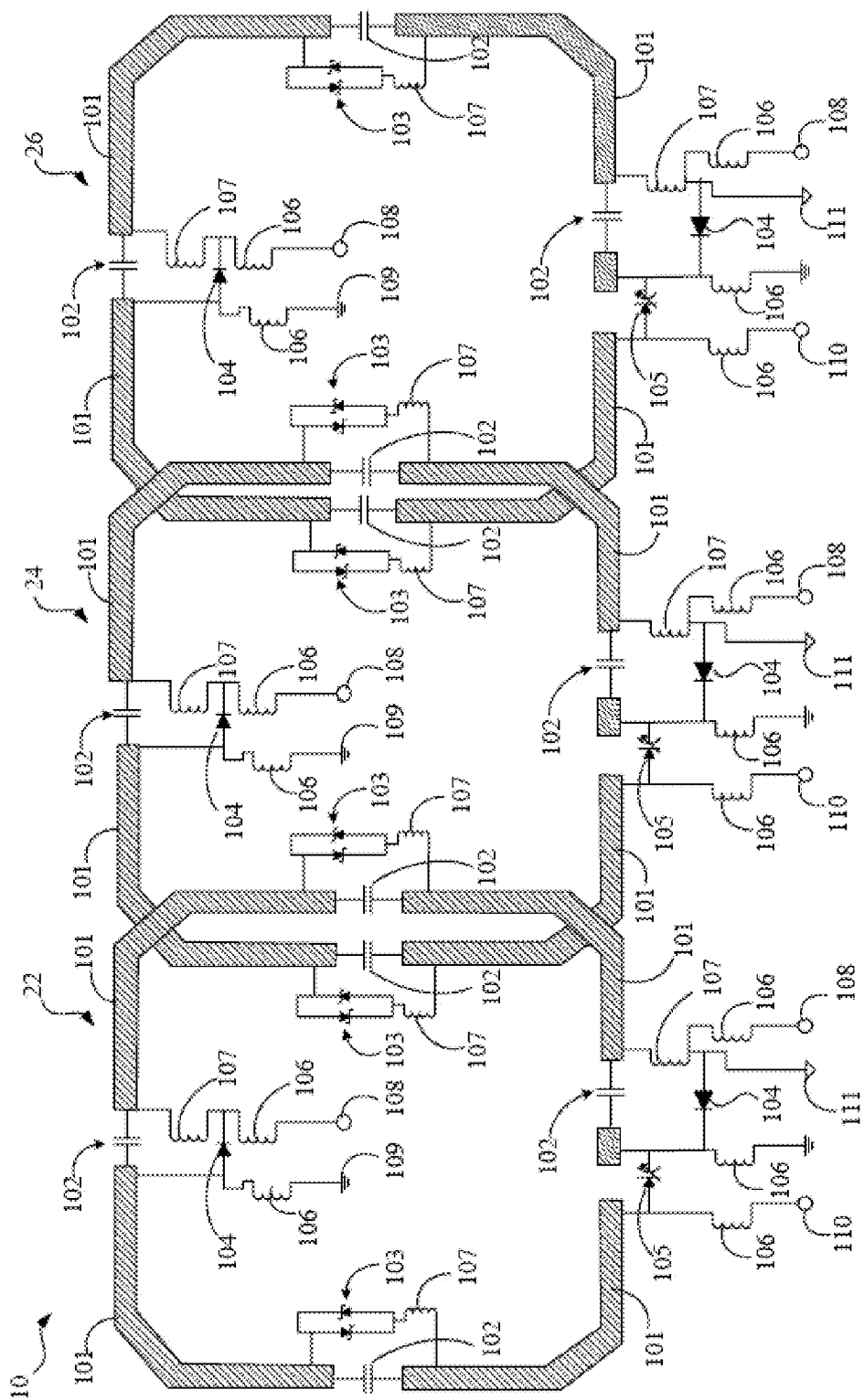
FIG. 5A is a circuit diagram of three overlapping circular surface coils.

An exemplary circuit design for eliminating inductive coupling in the coil array is shown in FIG. 4, FIG. 5A and FIG. 5B.

In FIG. 4, a single receive-only surface coil having a copper coil loop 101 is series connected with distributed capacitors 102 to resonate at the MRI Larmor frequency. The coil loop 101 is decoupled by active and passive circuits during high power radio frequency operation. The passive decoupling circuits include a zener diode 103, an inductor 107, and a capacitor 102. The active decoupling circuits, which include a PIN diode 104, the inductor 107 and the capacitor 102, are switched by a remote signal from an active decoupling port 108. The resonance frequency can be adjusted by applying a DC voltage from a tuning port 110 across a varactor 105. The varactor 105 is then switched to an LC resonant circuit to achieve a desired resonance frequency if frequency tuning is required. The use of a varactor 105 is well known by the skilled person in the art for implementing in the tuning circuit, and the implementation of the tuning circuit shown in the FIG. 4 is just one such embodiment. The entire tuning and decoupling control signal is series connected with the choke 106 to isolate the RF signal from alternating current (AC) when the circuits are connected to each remote control port such as active decoupling circuit and auto tuning circuit or when the circuits are connected with the ground 109.

Figure 6:
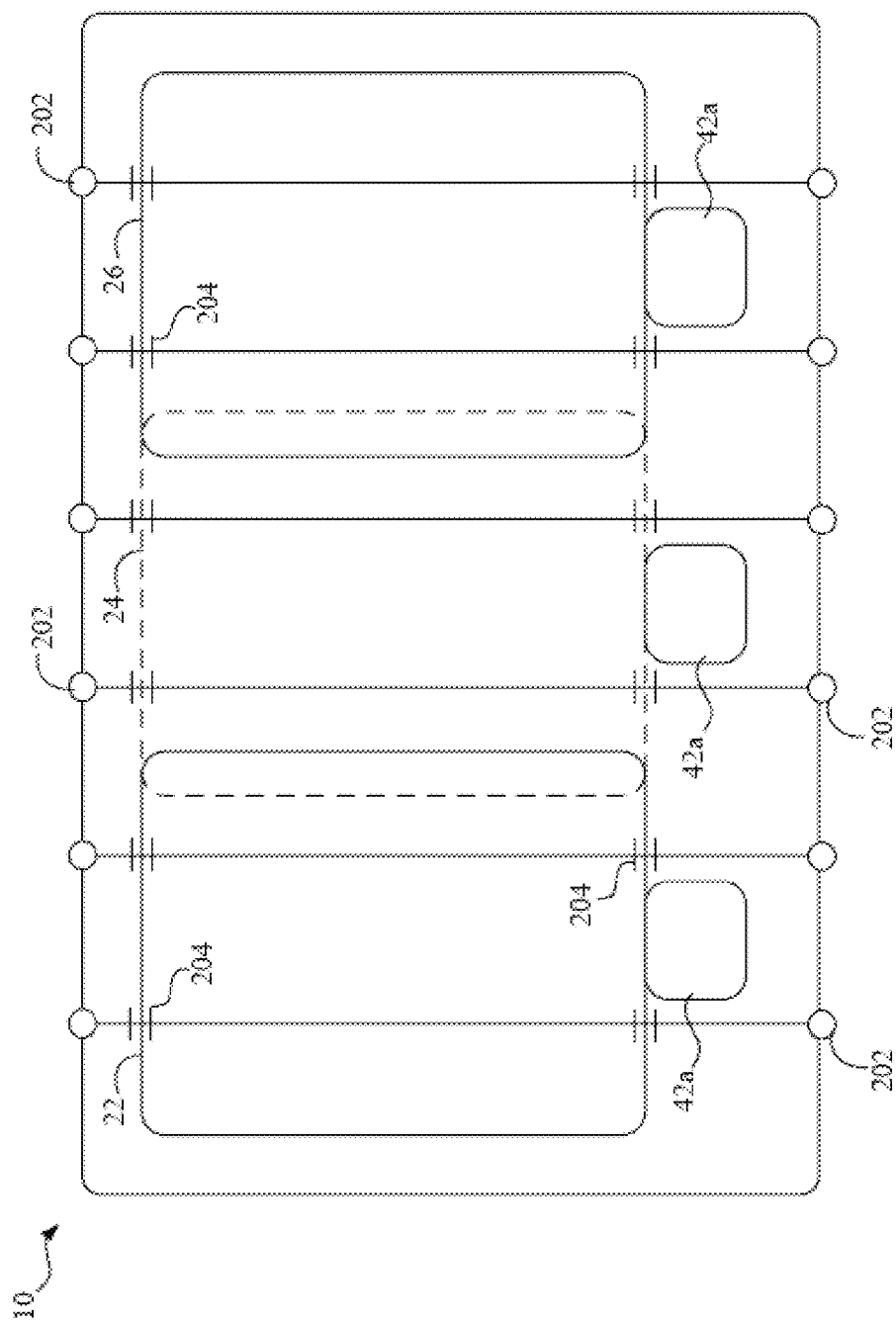
FIG. 6 is a plastic package of three circle surface coils.

A flexible coil is adjustable to accommodate subjects of different sizes, therefore maximizing coupling over a wide range of subject sizes, and minimizing the amount of external tuning required to match the coil output impedance to each preamplifier. The flexible phased array coil 10 as shown in FIG. 6 can be wrapped around the subject like a belt. The flexible phased array coil 10 in FIG. 6 includes three flexible rectangular coils 22, 24 and 26 that overlap to cancel mutual inductance. As shown in FIG. 6, the overlapped area includes a solid line and a dashed line as the overlap of two single coils, 22 and 24 or 24 and 26.

As shown in more detail in FIG. 5A, overlapped coils 22, 24 and 26 are identical to each other. The overlap areas in FIG. 5A show that pairs of coils are only inductively coupled, and not electrically coupled. However it should be noted that the overlap area, such as the overlap between coil 22 and coil 24, can be connected as shown in FIG. 5B, in which two coils 22 and 24 are connected by a DC controlled capacitor 112 and are controlled by the tuning port 110.

The coils are contained behind a plastic package to prevent direct contact with the human body. Similarly the entire active decoupling and auto tuning control circuit 42 in FIG. 4 is located in an open area 42a of FIG. 6 to connect to the remote control circuit. Referring back to FIG. 5A, the coil outputs 111 transmit output signals to each preamplifier. A pivot 202 links each plastic package and allows the flexible coil to bend to certain extents.

Figure 7:
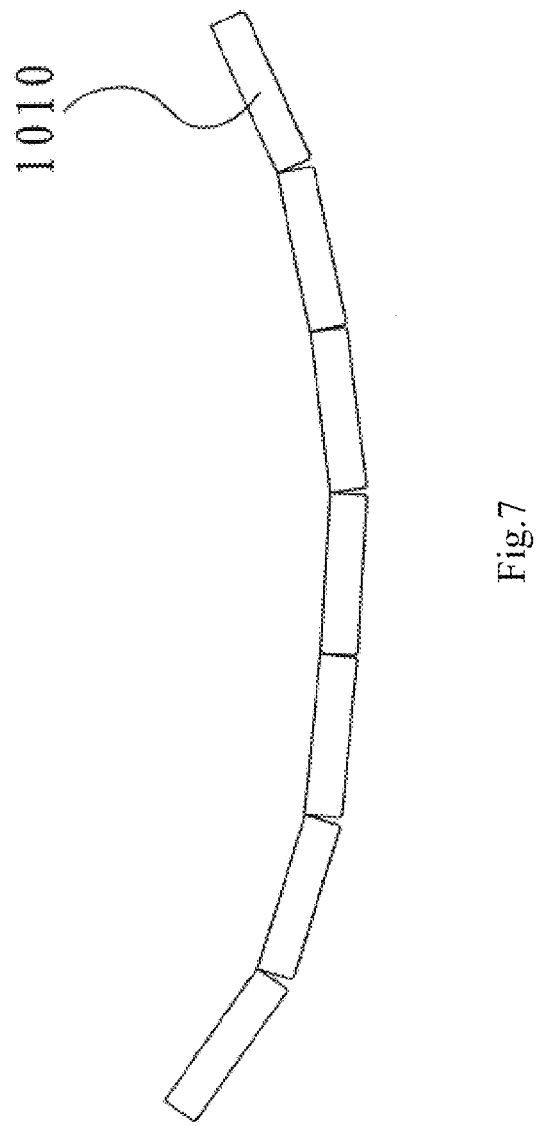
FIG. 7 is a side view of a flexible phased array coil.
Figure 8:
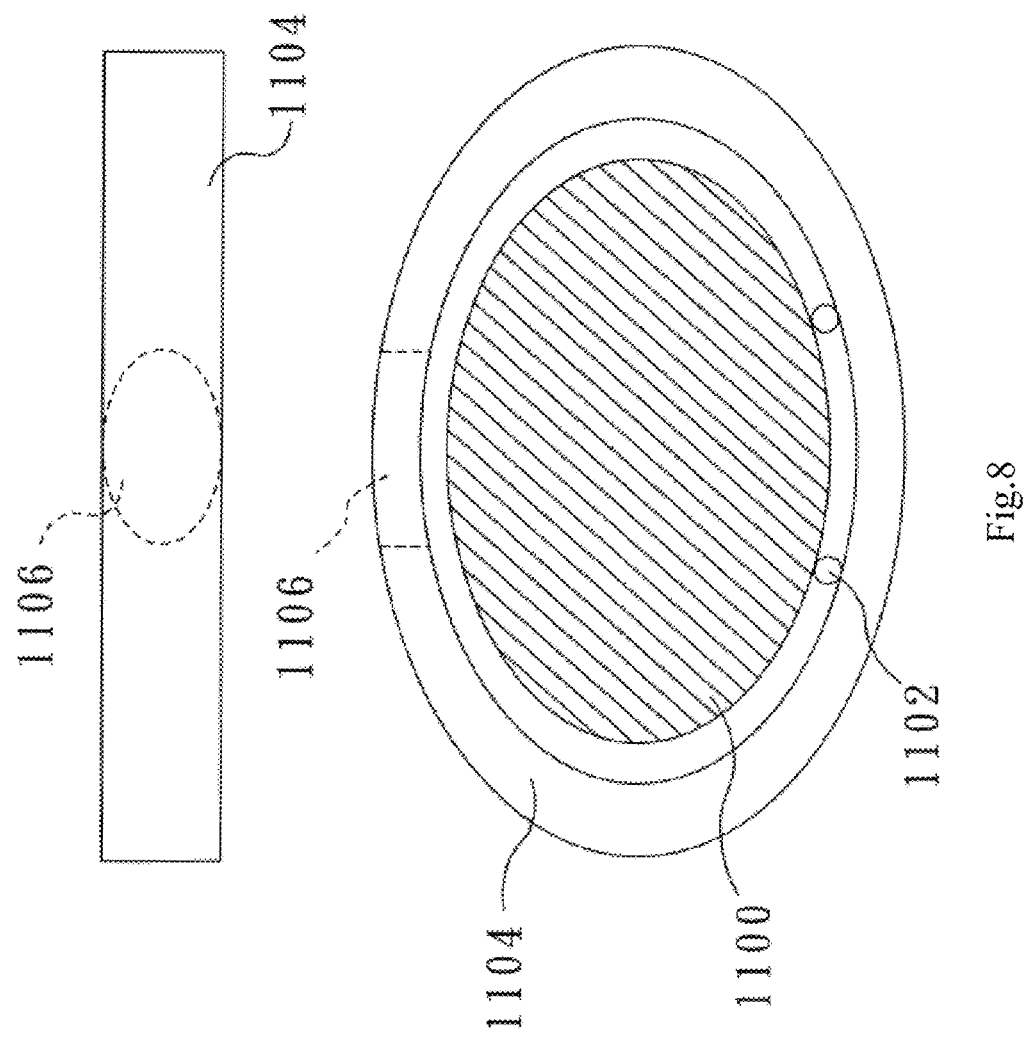
FIG. 8 is an illustration of a coil belt for placement around or partially around a human torso.
Figure 9:
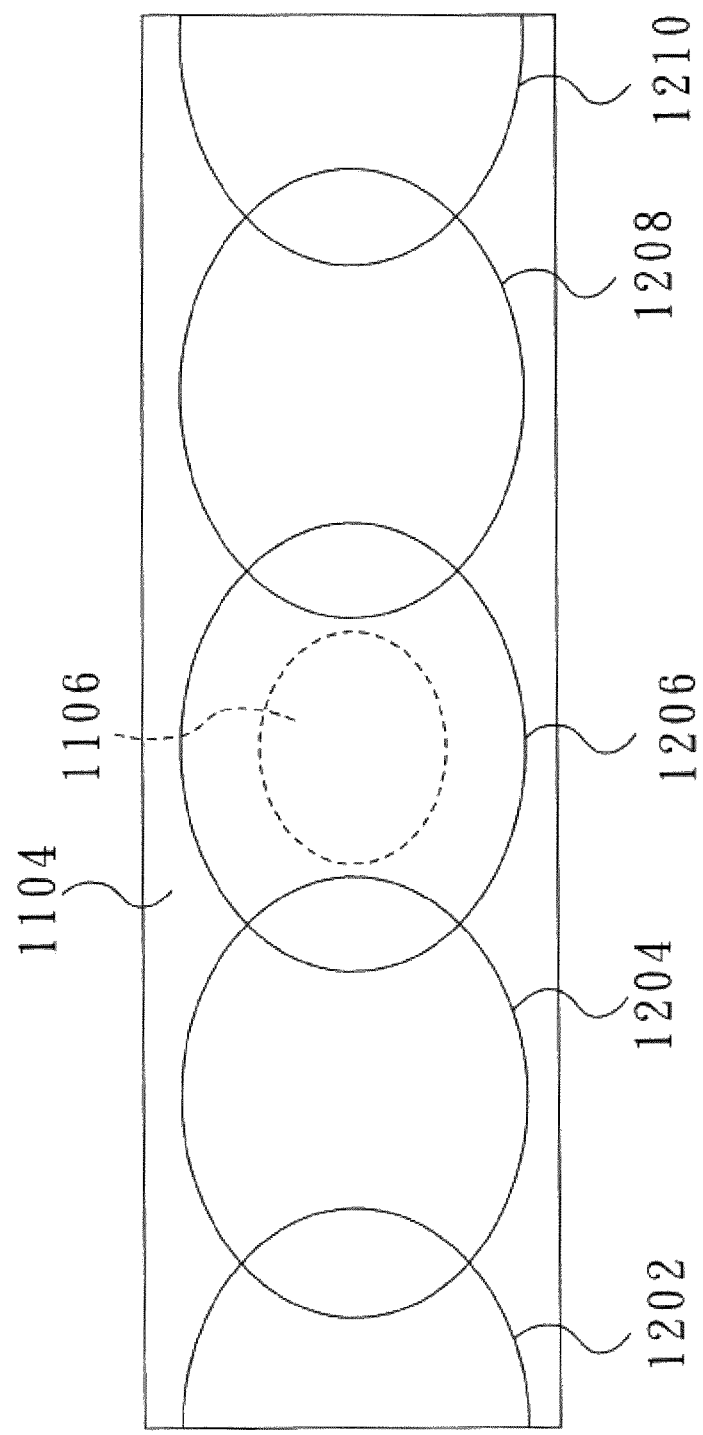
FIG. 9 is a upper view of the coil belt in FIG. 8.

The flexible phased array coil defines a belt 1104 that can wrap around a portion of a body, as shown in side view in FIG. 7, or even wrap all the way around a body trunk 1100 as shown in FIG. 8. The belt 1104 has a belt hole 1106, similar to the center hole of the surface coil 120, through which the HIFU transducer 280 passes. The belt 1104 can be rotated on a ball 1102 located between the belt 1104 and the body trunk 1100. In its unbent configuration, the belt 1104 appears as shown in FIG. 9. The belt 1102 includes three full coils 1204, 1206 and 1208 and two half coils 1202 and 1210, with the belt hole 1106 being located in coil 1206. The two half coils 1202, 1210 form one full coil when the belt 1104 is wrapped.

The apparatus described herein, which combines the advantages of MRI imaging and a non-invasive therapy procedure, requires a fast imaging method to reduce acquisition times. Parallel MRI techniques accelerate image acquisition by extracting spatial information from the sensitivity patterns of RF coil arrays and substituting that information for a portion of data that would normally be acquired from a gradient field pulse sequence. Therefore the use of a small focal coil in the anterior and a flexible phased array not only improves image quality at the point of treatment but also allows for speed improvement via parallel imaging. In the case of parallel imaging, a controller unit would receive real-time MRI images and, based on that image's information, guide the therapeutic device in performing a medical procedure in real-time, or transform the MRI images into a reference to provide assistance in the performance of the medical procedure.

Having described the invention, and a preferred embodiment thereof, what is claimed as new, and secured by Letters Patent is:

1. A magnetic resonance imaging and treatment system comprising:
    a table;
    a first RF (radio frequency) coil having a center hole, movably disposed over the table;
    a second RF coil, movably disposed on the table;
    a high-intensity focused ultrasound transducer having a head configured to pass through the center hole of the first RF coil, wherein the high-intensity focused ultrasound transducer is configured to move together with the first RF coil;
    wherein said second RF coil is larger than said first RF coil in size, so that said second RF coil has a larger field of view than said first RF coil, and said second RF coil is separate from said first RF coil; and
    wherein both of the first RF coil and the high-intensity focused ultrasound transducer are capable of movement relative to the second RF coil.

2. The magnetic resonance imaging and treatment system of claim 1, wherein the first RF coil is a surface coil and the second RF coil is a flexible coil.

3. The magnetic resonance imaging and treatment system of claim 1, wherein said second RF coil comprises a phased array coil.

4. The magnetic resonance imaging and treatment system of claim 1, further comprising a decoupling circuitry to eliminate coupling between said first RF coil and said second RF coil.

5. The magnetic resonance imaging and treatment system of claim 1, wherein said first RF coil and said second RF coil comprise at least a single loop.

6. The magnetic resonance imaging and treatment system of claim 1, wherein said second RF coil comprises an array of coils forming a belt.

* * * * *